(12) United States Patent
Lim et al.

(10) Patent No.: US 10,463,483 B2
(45) Date of Patent: Nov. 5, 2019

(54) MINIMALLY INVASIVE MITRAL VALVE REPLACEMENT WITH BRIM

(71) Applicant: Venus Medtech (Hangzhou), Inc., Hangzhou, Zhejiang (CN)

(72) Inventors: Hou-Sen Lim, Regensburg (DE); Wolfgang Gotz, Regensburg (DE)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 169 days.

(21) Appl. No.: 15/623,790

(22) Filed: Jun. 15, 2017

(65) Prior Publication Data

US 2017/0281341 A1 Oct. 5, 2017

Related U.S. Application Data

(63) Continuation of application No. PCT/EP2015/080582, filed on Dec. 18, 2015.

(30) Foreign Application Priority Data

| Dec. 19, 2014 | (EP) | .................................... 14199488 |
| Dec. 23, 2014 | (EP) | ..................................... 1419956 |
| Dec. 18, 2015 | (WO) | ................. PCT/EP2015/080582 |

(51) Int. Cl.
*A61F 2/24* (2006.01)

(52) U.S. Cl.
CPC .......... *A61F 2/2418* (2013.01); *A61F 2/2439* (2013.01); *A61F 2210/0014* (2013.01); *A61F 2220/0008* (2013.01); *A61F 2250/006* (2013.01); *A61F 2250/0006* (2013.01)

(58) Field of Classification Search
CPC ........ A61F 2/24; A61F 2/2418; A61F 2/2439; A61F 2/2469; A61F 2/2409; A61F 2002/8483
See application file for complete search history.

(56) References Cited

U.S. PATENT DOCUMENTS

| 6,458,153 B1 * | 10/2002 | Bailey ................... A61F 2/2418 |
| | | 623/1.24 |
| 6,695,878 B2 * | 2/2004 | McGuckin, Jr. ............................. |
| | | A61B 17/12109 |
| | | 606/153 |
| 7,195,641 B2 * | 3/2007 | Palmaz ................. A61F 2/2418 |
| | | 623/1.26 |

(Continued)

FOREIGN PATENT DOCUMENTS

| WO | WO 2008/029296 | 3/2008 |
| WO | WO 2013/059743 | 4/2013 |
| WO | WO 2014/144937 | 9/2014 |

*Primary Examiner* — Alvin J Stewart
(74) *Attorney, Agent, or Firm* — Raymond Sun (57) ABSTRACT

A collapsible-expandable tubular stent (29) constructed of shape-memory material which is implantable into a human heart, which comprises proximal and distal rings (71, 73) and at least two spaced apart posts (69) that extend axially between said rings (71, 73), said distal ring (73) comprising a plurality of distal arms (77) which are connected to the distal ring (73) at only one end and which have a free opposite end; said proximal ring (71) comprising a plurality of, which are connected at only one end to the proximal ring (71) and which have a free opposite end, which proximal arms (75) are constructed to swing radially outward at their free ends.

12 Claims, 5 Drawing Sheets

(56) References Cited

U.S. PATENT DOCUMENTS

| | | | | |
|---|---|---|---|---|
| 7,201,772 B2* | 4/2007 | Schwammenthal | A61F 2/2418 | 623/1.24 |
| 7,837,727 B2* | 11/2010 | Goetz | A61F 2/2418 | 623/1.15 |
| 7,947,075 B2* | 5/2011 | Goetz | A61F 2/2418 | 623/1.15 |
| 8,449,599 B2* | 5/2013 | Chau | A61F 2/2418 | 623/1.26 |
| 8,579,964 B2* | 11/2013 | Lane | A61F 2/2418 | 623/2.11 |
| 8,652,203 B2* | 2/2014 | Quadri | A61F 2/2418 | 623/2.11 |
| 9,439,763 B2* | 9/2016 | Geist | A61F 2/2466 | |
| 9,480,560 B2* | 11/2016 | Quadri | A61F 2/2418 | |
| D800,908 S * | 10/2017 | Hariton | D24/155 | |
| 10,117,744 B2* | 11/2018 | Ratz | A61F 2/2418 | |
| 10,179,044 B2* | 1/2019 | Ratz | A61F 2/2418 | |
| 2009/0005863 A1* | 1/2009 | Goetz | A61F 2/2418 | 623/2.18 |
| 2010/0174359 A1* | 7/2010 | Hefti | A61F 2/2412 | 623/1.26 |
| 2010/0204781 A1* | 8/2010 | Alkhatib | A61F 2/2418 | 623/1.26 |
| 2010/0249894 A1* | 9/2010 | Oba | A61F 2/2418 | 623/1.11 |
| 2010/0256723 A1* | 10/2010 | Murray | A61F 2/2418 | 623/1.2 |
| 2011/0022157 A1* | 1/2011 | Essinger | A61F 2/2418 | 623/1.26 |
| 2011/0029072 A1* | 2/2011 | Gabbay | A61F 2/2409 | 623/2.23 |
| 2011/0040366 A1* | 2/2011 | Goetz | A61F 2/2418 | 623/1.12 |
| 2011/0040374 A1* | 2/2011 | Goetz | A61F 2/2418 | 623/2.11 |
| 2011/0098800 A1* | 4/2011 | Braido | A61F 2/2412 | 623/1.16 |
| 2011/0238159 A1* | 9/2011 | Guyenot | A61F 2/2418 | 623/1.26 |
| 2011/0245911 A1* | 10/2011 | Quill | A61F 2/2418 | 623/1.26 |
| 2011/0306916 A1* | 12/2011 | Nitzan | A61F 2/2418 | 604/9 |
| 2011/0319991 A1* | 12/2011 | Hariton | A61F 2/2412 | 623/2.14 |
| 2012/0078353 A1* | 3/2012 | Quadri | A61F 2/2418 | 623/2.11 |
| 2012/0215303 A1* | 8/2012 | Quadri | A61F 2/2418 | 623/2.18 |
| 2013/0018449 A1* | 1/2013 | Bailey | A61F 2/2418 | 623/1.11 |
| 2013/0018458 A1* | 1/2013 | Yohanan | A61F 2/2418 | 623/2.18 |
| 2013/0096664 A1* | 4/2013 | Goetz | A61F 2/2418 | 623/1.11 |
| 2013/0096670 A1* | 4/2013 | Goetz | A61F 2/2418 | 623/1.16 |
| 2013/0131788 A1* | 5/2013 | Quadri | A61F 2/2412 | 623/2.4 |
| 2013/0204359 A1* | 8/2013 | Thubrikar | A61F 2/2415 | 623/2.17 |
| 2013/0253643 A1* | 9/2013 | Rolando | A61F 2/2445 | 623/2.37 |
| 2013/0304200 A1* | 11/2013 | McLean | A61F 2/2427 | 623/2.18 |
| 2014/0005778 A1* | 1/2014 | Buchbinder | A61F 2/2445 | 623/2.18 |
| 2014/0025164 A1* | 1/2014 | Montorfano | A61F 2/2409 | 623/2.37 |
| 2014/0052237 A1* | 2/2014 | Lane | A61F 2/2412 | 623/2.11 |
| 2014/0081389 A1* | 3/2014 | Chau | A61F 2/2418 | 623/2.11 |
| 2014/0249622 A1* | 9/2014 | Carmi | A61F 2/2442 | 623/2.11 |
| 2014/0257467 A1* | 9/2014 | Lane | A61F 2/2412 | 623/2.11 |
| 2014/0277390 A1* | 9/2014 | Ratz | A61F 2/2418 | 623/1.26 |
| 2014/0277427 A1* | 9/2014 | Ratz | A61F 2/2409 | 623/2.38 |
| 2014/0358224 A1* | 12/2014 | Tegels | A61L 27/14 | 623/2.14 |
| 2015/0112430 A1* | 4/2015 | Creaven | A61F 2/2436 | 623/2.11 |
| 2015/0142100 A1* | 5/2015 | Morriss | A61F 2/2418 | 623/2.4 |
| 2015/0142101 A1* | 5/2015 | Coleman | A61F 2/2457 | 623/2.11 |
| 2015/0148731 A1* | 5/2015 | McNamara | A61B 17/0057 | 604/9 |
| 2015/0196390 A1* | 7/2015 | Ma | A61F 2/2418 | 623/2.17 |
| 2015/0216661 A1* | 8/2015 | Hacohen | A61B 17/0401 | 623/2.37 |
| 2015/0351903 A1* | 12/2015 | Morriss | A61F 2/2418 | 623/2.11 |
| 2015/0351904 A1* | 12/2015 | Cooper | A61F 2/2418 | 623/2.1 |
| 2016/0008131 A1* | 1/2016 | Christianson | A61F 2/2418 | 623/2.11 |
| 2016/0081799 A1* | 3/2016 | Leo | A61F 2/2418 | 623/1.18 |
| 2016/0106539 A1* | 4/2016 | Buchbinder | A61F 2/2418 | 623/2.19 |
| 2016/0193044 A1* | 7/2016 | Achiluzzi | A61F 2/2409 | 623/2.11 |
| 2018/0206986 A1* | 7/2018 | Noe | A61F 2/2445 | |

* cited by examiner

MINIMALLY INVASIVE MITRAL VALVE REPLACEMENT WITH BRIM

FIELD OF THE INVENTION

The present invention relates to a prosthetic valve for implantation in the heart in a minimally invasive or percutaneous manner, and more particularly to a prosthetic heart valve suitable for replacement of a mammal heart valve, most particularly an atrio-ventricular valve, a mitral valve and a tricuspid valve.

BACKGROUND OF THE INVENTION

Four valves in the heart serve to direct the flow of blood through the two sides of the heart in a forward direction. The mitral valve, located between the left atrium and the left ventricle, and the aortic valve, located between the left ventricle and the aorta, constitute the systemic portion of the heart. These two valves direct oxygenated blood coming from the lungs through the left side of the heart into the aorta for distribution throughout the body. The right side of the heart includes the tricuspid valve, located between the right atrium and the right ventricle, and the pulmonary valve, located between the right ventricle and the pulmonary artery. These two valves direct de-oxygenated blood returning from the body through the right side of the heart into the pulmonary artery for distribution to the lungs, where it again becomes re-oxygenated to begin its circuit anew.

Heart valves are passive structures having leaflets that simply open and close in response to differential pressures on either side of the particular valve. The mitral valve has two leaflets and the tricuspid valve has three. The aortic and pulmonary valves are sometimes referred to as semilunar valves because of the appearance of their three leaflets; these leaflets are shaped somewhat like a half-moon and are sometimes termed cusps.

The leaflets and surrounding elements of each valve vary with the function of the heart it supports. The atrioventricular valves, otherwise known as mitral (in the left chamber of the heart) and tricuspid (in the right chamber of the heart), are generally a continuum extending from the myocardium or muscular wall of the lower chambers, through the papillary muscles, to which is attached a confluence of tendinous rope-like elements, known as chordae tendineae, that are attached to the edges and undersurface of the differently shaped leaflets which open to allow flow and close to stop flow. The leaflets terminate at a ring-like structure usually known as an annulus, which is part of the fibrous skeleton of the heart.

When the left ventricular wall relaxes, the ventricular chamber enlarges and draws in blood from the atrium as the leaflets of the mitral valve separate, opening the valve. Oxygenated blood flows in a downward direction through the valve, to fill the expanding ventricular cavity. Once the left ventricular cavity has filled, the left ventricle contracts, causing a rapid rise in the left ventricular cavity pressure. This causes the mitral valve to close and opens the aortic valve, allowing oxygenated blood to be ejected from the left ventricle into the aorta. The chordae tendineae of the mitral valve prevent the mitral leaflets from prolapsing back into the left atrium when the left ventricular chamber contracts. The three leaflets, chordae tendineae, and papillary muscles of the tricuspid valve function in a similar manner, in response to the filling of the right ventricle and its subsequent contraction.

The cusps of the aortic valve respond passively to pressure differentials between the left ventricle and the aorta. When the left ventricle contracts, the aortic valve cusps open to allow the flow of oxygenated blood from the left ventricle into the aorta. When the left ventricle relaxes, the aortic valve cusps reassociate to prevent blood, which has entered the aorta from leaking (regurgitating) back into the left ventricle. The pulmonary valve cusps respond passively in the same manner in response to relaxation and contraction of the right ventricle in moving de-oxygenated blood into the pulmonary artery and thence to the lungs for re-oxygenation. These semilunar valves do not require associated chordae tendineae or papillary muscles.

Stenosis is one problem that heart valves may develop in which a valve does not open properly, another is insufficiency, or regurgitation, where a valve fails to close properly. In addition, a bacterial or fungal infection may require that a heart valve be surgically repaired or replaced. Sometimes such a problem can be treated by surgical repair of a valve; however, often a valve is too diseased to repair and must be replaced. If a heart valve must be replaced, there are currently several options available, and the choice of a particular type of artificial valve depends on factors including the location of the valve, the age and other specifics of the patient, and the particular surgeon's experiences and preferences.

Replacement heart valves or heart valve prostheses have been produced for more than four decades. Such valves have been made from a variety of materials of biologic and artificial nature; as a result two distinct categories of the prostheses have evolved: biological and mechanical prosthetic heart valves. Mechanical or artificial valves are typically constructed from non-biological materials, such as plastics, metals and other artificial materials which, while durable, are prone to blood clotting which increases the risk of an embolism. Anticoagulants which may be taken to prevent blood clotting can possibly complicate a patient's health due to increased risk of hemorrhage.

Biological or tissue valves are constructed from animal tissue, such as bovine, equine or porcine tissue, although some efforts have been made at using tissue from a patient for which the valve will be constructed. Tissue valves are often constructed by sewing leaflets of pig aortic valves to a stent to hold the leaflets in proper position, or by constructing valve leaflets from the pericardial sac of cows, horses or pigs and sewing them to a stent. The pericardium is a membrane that surrounds the heart and isolates it from the rest of the chest wall structures. Such porcine, equine or bovine tissue is chemically treated to alleviate antigenicity and to make them more durable. Additional treatments may be applied to avoid structural valve deterioration in the long-term due to calcification. One main advantage of tissue valves is that they do not cause blood clots to form as readily as do the mechanical valves; therefore, they do not absolutely require life-long systemic anticoagulation. The major disadvantage of tissue valves is that they lack the long-term durability of mechanical valves.

Various surgical techniques that have been used to repair a regurgitant or damaged mitral valve include annuloplasty, quadrangular resection (narrowing the valve leaflets), and commissurotomy (cutting the valve commissures to separate the valve leaflets). The most common treatment for mitral stenosis and diseased aortic valve has been the replacement of an affected valve by a prosthetic valve via open-heart surgery by excising the valve leaflets of the natural valve and securing a replacement valve in the valve position, usually by suturing the replacement valve to the natural valve annulus. In instances where a patient is deemed operable only at too high a surgical risk, one alternative in valve stenosis has been to dilate the native valve with a balloon catheter to enlarge the valve orifice; however, such practice has experienced a high restenosis rate.

Generally, it would be desirable if heart valves could be replaced using minimally invasive techniques. Proposals have been made to remove a defective heart valve via an endovascular procedure, that is, a procedure where the invasion into the body is through a blood vessel, such as the femoral artery, and is carried out percutaneously and transluminally using the vascular system to convey appropriate devices to the particular body position to carry out the desired procedure. Angioplasty is also an example of such a procedure wherein a catheter carrying a small balloon at its distal end is manipulated through the body's vessels to a point where there is a blockage in a vessel. The balloon is expanded to create an opening in the blockage, and then deflated; the catheter and balloon are then removed. Such endovascular procedures have substantial benefits both from the standpoint of health and safety as well as cost. Such procedures require minimal invasion of the human body, and there is consequently considerable reduction and in some instances even elimination, of the use of a general anesthesia and much shorter hospital stays.

U.S. Pat. No. 7,837,727 B2 to present applicant, the disclosure of which is incorporated herein by reference, discloses an aortic heart valve prosthesis that can be implanted in the body by use of a catheter. The valve prosthesis includes a support structure or tubular stent with a tissue valve connected to it that is delivered in a collapsed shape through a blood vessel. The prosthesis is delivered to a location near the patient's native aortic valve and then expanded from its collapsed configuration to a deployed configuration. It is secured in expanded condition at a desired location in a blood vessel, e.g. downstream for the aortic valve.

A variety of arrangements are described for deploying prostheses of various shapes and designs for aortic valves so that the prosthesis becomes implanted interiorly of the three native leaflets of the aortic valve, which are compressed radially outwardly.

Systems of this general type have shown promise and are considered to be attractive and accordingly, efforts are continuing to produce improvements in such prosthetic valves that can be minimally invasively implanted.

Overall, the use of a minimally invasive approach has a great number of advantages; an endovascular approach is generally used. However, there is only limited space available within the vasculature; thus, the surgical field is often only as large as the diameter of a blood vessel. Consequently, the introduction of tools and prosthetic devices becomes greatly complicated, and the device to be implanted must be dimensioned and configured to permit it to be introduced into the vasculature, maneuvered therethrough, and then positioned at a desired location. In the majority of aged patients suffering from aortic stenosis, the aortic vessel and aortic arch are affected by calcified atheromatous plaques. Delivery of bulky tools and prosthetic devices retrograde through an atheromatous aortic vessel has increased risk of injuring of the atheromatous aortic wall with subsequent potential embolism and even aortic wall rupture.

In spite of all improvements achieved in the field of aortic valve replacement, there is still a lack in promising mitral valve replacement techniques and suitable mitral valve devices.

SUMMARY OF THE INVENTION

Therefore, it could be one object to provide a valve, in particular a mitral valve, and a delivery system for delivering the prosthetic valve to a patient's heart configured to be releasably folded or crimped inside a lumen of or on the delivery system through a percutaneous intercostal penetration of a patient's chest and wall of the heart's left ventricle, left or right atrium, or, preferably, through an opening at a jugular vein, subclavian vein, femoral vein and other blood vessel.

It is one aspect of the present invention to provide a prosthetic mitral heart valve with an expandable-collapsible support structure or tubular stent having sufficient flexibility to permit repositioning the valve after its initial placement by reversion to a fully or partially collapsed stage before final placement. The reversion may be achieved by means of stings releasably attached to the tubular stent of the heart valve as is describe, e. g., in U.S. Pat. No. 7,837,727 B2, the disclosure of which is incorporated herein by reference.

It is one aspect of the present invention to provide a collapsible-expandable tubular stent comprising or constructed of shape-memory material which is implantable into a human heart. The tubular stent comprises a first ring called proximal ring and a second ring arranged distal to the proximal ring and called a distal ring hereinafter.

The stent also comprises at least two spaced apart posts that extend axially between said rings. The posts may extend in a longitudinal direction of the tubular stent.

The distal ring comprises a plurality of arms which are called distal arms hereinafter and which are connected to the distal ring at only one end of the arm and/or which have a free opposite end that is not fixed to the distal ring.

The proximal ring comprises a plurality of arms which are called proximal arms hereinafter and which are connected at only one end of the arm to the proximal ring and/or which have a free opposite end that is not fixed to the proximal ring. The proximal arms are constructed to extend outwardly with their free ends, or to swing radially outward at their free ends, or to move radially outward, in particular when first put in parallel with a longitudinal axis of the tubular stent by means of an radially inwardly acting force with the force then being released, or to exert from the longitudinal axis of the tubular stent by an angle of preferably about 70° or between 60° and 105°, more preferably between 60° and 85°.

It is another aspect of the present invention to provide a heart valve comprising a tubular stent according to the present invention. The tubular stent is interconnected to a plurality of flexible leaflets disposed on or in particular interior of said stent, which leaflets open to permit blood flow in a downstream direction and close to prevent blood flow in an upstream direction therethrough.

Embodiments of the present invention can include additionally or alternatively one or more of the preceding and/or following features independently of any other feature, i. e., without having to comprise any other feature in combination as well.

Whenever the expression "can", "may be" or "may have", and so on is used herein, it is to be understood synonymously with "in exemplary embodiments is" or "in exemplary embodiments has", "preferably is" or "preferably has" respectively, and so on, and is intended to illustrate exemplary embodiments.

In the following, the expression "distal end" may be understood as the end of the implantation device or of a receiving device for the implant (such as a delivery catheter), which is intended to be inserted. The expression "proximal end" may be understood as the end of the implantation device or receiving device opposite to the distal end, in other words, the end, which will be orientated to and manipulated by a surgeon or operator.

Whenever numerical values are mentioned herein such as "one", "two" and the like, they have to be understood as values representing the lower threshold of numerical ranges. A long as this does not result in a contradiction in the eyes of the skilled one, numerical values, such as "one" shall be understood as comprising also "at least one". This interpretation or understanding is as well encompassed by the present invention as the understanding according to which a numerical value such as "one" may be understood as "exactly one" whenever this appears technically possible to the skilled person. Both understandings are covered by the present invention. This applies to any numerical value stated herein.

In some exemplary embodiments according to the present invention the distal arms are connected to the distal end or distal tips of the distal ring or integral therewith. Preferably, they are connected or integral with the distal ring exclusively by the distal end of the distal ring or distal tips of an undulating pattern of the ring.

In certain exemplary embodiments according to the present invention the proximal arms are connected to the proximal end or proximal tips of the proximal ring or integral therewith. Preferably, they are connected or integral with the proximal ring exclusively by the proximal end of the proximal ring or proximal tips of an undulating pattern of the proximal ring.

In some exemplary embodiments according to the present invention at least some of said distal arms and/or some of the proximal arms have means at its said free opposite end which allows attachment of strings to individually control and/or retract some or each of said arms.

In certain exemplary embodiments according to the present invention, some or all of adjacent distal arms are not interlinked with or connected to each other. In these embodiments, they are in contact with each other only be way of the undulating structure of the distal ring or by cover material or other material that does not form the tubular stent. In some exemplary embodiments, this applies also to the proximal arms of the proximal ring.

Figures 2, 3:
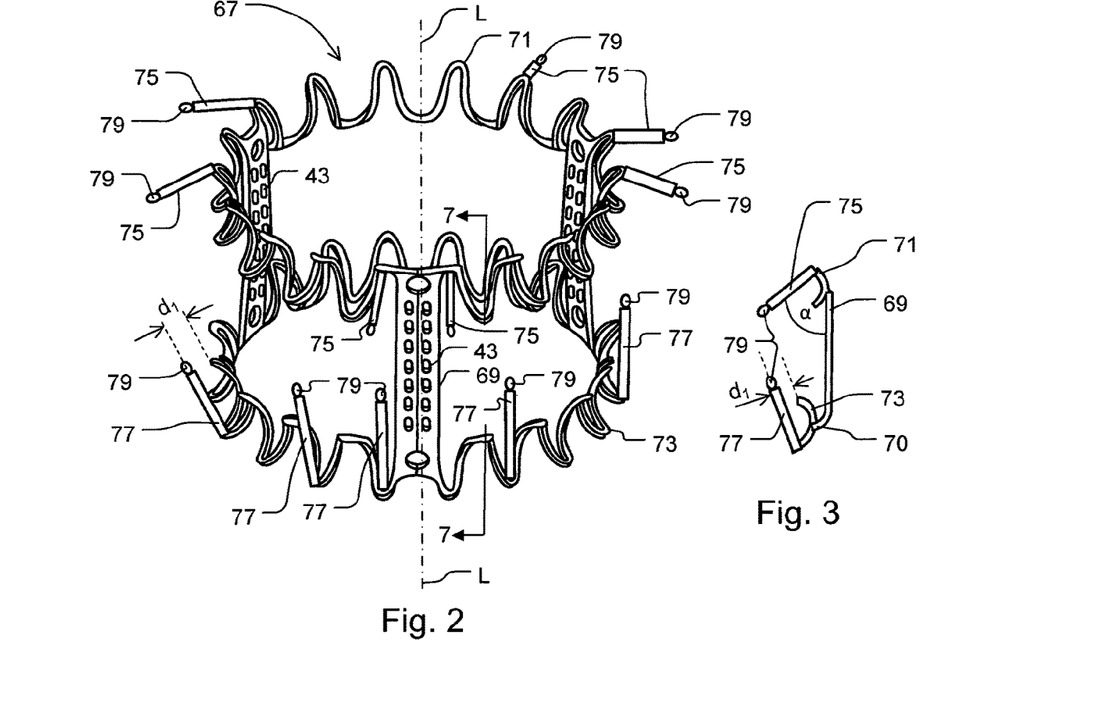
FIG. 2 is a perspective view of the stent of FIG. 1 shown in its expanded orientation.
FIG. 3 is a cross-sectional view taken generally along the line 7-7 of FIG. 2.

In certain exemplary embodiments according to the present invention all or at least some of said proximal arms are intended to assume a more or less rectangular position with regard to a longitudinal axis of the tubular stent by their shape-memory capacity, preferably between 60° and 85° (see angle α in FIG. 3).

In some exemplary embodiments according to the present invention at least some of said proximal arms are interconnected to a brim of biocompatible material, preferably of biocompatible sheet material.

In certain exemplary embodiments according to the present invention said collapsible-expandable tubular stent is integrally formed or forms one single piece. In particular, it does not comprise a separate envelope made of shape-memory material or other material.

In some exemplary embodiments according to the present invention the leaflets are arranged so as to form a first cusp, a second cusp and a third cusp, for example as cuspis anterior, cuspis posterior, cuspis septalis.

In certain exemplary embodiments according to the present invention the tubular stent is connected with an exterior covering of biocompatible sheet material surrounding the posts.

In some exemplary embodiments according to the present invention said heart valve is a mitral heart valve.

In certain exemplary embodiments according to the present invention the heart valve is a bioprosthetic or prosthetic heart valve.

In some exemplary embodiments according to the present invention said proximal and distal rings are undulating wires or structures formed of a material having a flexibility that allows collapsing and expanding to change the diameter of the rings.

In certain exemplary embodiments according to the present invention said rings have a memory that causes them to expand to a larger diameter at or by the temperature within the human body when radially unrestrained.

In some exemplary embodiments according to the present invention three equiangularly spaced longitudinal posts are provided which are integral at their ends with said proximal and distal rings.

In some exemplary embodiments according to the present invention some or each of said posts have apertures located near its distal and proximal ends, through which apertures strings can be passed to exert radially inward force to maintain said stent in a collapsed orientation or state.

In some exemplary embodiments according to the present invention an exterior covering of biocompatible sheet material surrounds said tubular stent.

In some exemplary embodiments according to the present invention the tubular stent is formed from a continuous strand of shape-memory alloy wire wound into a plurality of sinuous or undulating loops.

In certain exemplary embodiments according to the present invention the tubular stent is provided with its distal and proximal arms so as to be anchored within the heart by the distal arms that hook to the free leaflet edge and/or chordae tendineae on one side and the brim at the native valve annulus on the other side creating the counteracting force to the distal arms. That way, the stent-body may be restrained between leaflet free edge (chordac) and the mitral valve annulus. The brim may create a force that is pulling the tubular stent in direction of the left atrium, the distal arms prevent the stent from moving into the direction of the left atrium. That way, the tubular stent may appears like a rivet or a bolt within the annulus.

In some exemplary embodiments according to the present invention there is a gap or smallest distance between the outer or most radial end of the proximal tip or tips of the distal ring and the distal arms. The ring and the arms are provided such that the gap does not (or not substantially) change or is not meant or intended to change upon crimping or deploying. Hence, the gap is—at least more or less—maintained while implanting the valve comprising the tubular stent.

In certain exemplary embodiments according to the present invention the distal ring, or the particular undulations that form the distal ring, is arranged such that it be tilted or rotated about an imaginary rotation axis that is preferably perpendicular to the longitudinal axis of the tubular body.

In exemplary embodiments according to the present invention, some of the advantages mentioned herein can be achieved.

The present invention discloses a minimally invasive system for facilitating intervention within the heart or great vessels without the need for a median sternotomy or other form of gross thoracotomy in order to try to substantially reduce trauma, risk of complications, recovery time, and pain for the patient. The surgical procedure is not endovascular, but is performed through percutaneous penetrations within intercostal spaces of the patient's rib cage. Alternatively, it is carried out by means of a vein, for example transfemorally.

To repair or replace the mitral valve, a conventional procedure for approaching the left atrium has been employed by the use of intravascular catheterization from a femoral vein through the intraatrial septum, which separates the right atrium and the left atrium.

Another advantage of the present invention is, when mounting a valve into or onto a tube it is better to have three, or possibly more, leaflets than only two. When making two leaflets only, the leaflets' free edge length is equal to the diameter of the valve which does not allow the leaflets to open up much and to provide a large opening orifice. Rather, the resulting orifice is just a slit. However, when providing three leaflets, the valve leaflets free edge can open up widely, creating a large and possibly circular orifice upon opening. Thus providing three leaflets has physical, mechanical and fluid dynamic reasons equal to the situation in the aortic valve. In contrast, the native mitral valve can work with only two leaflets only since the two leaflets work like two sails but not like cusps in the aortic valve.

DETAILED DESCRIPTION OF THE PREFERRED EMBODIMENTS

Figure 1:
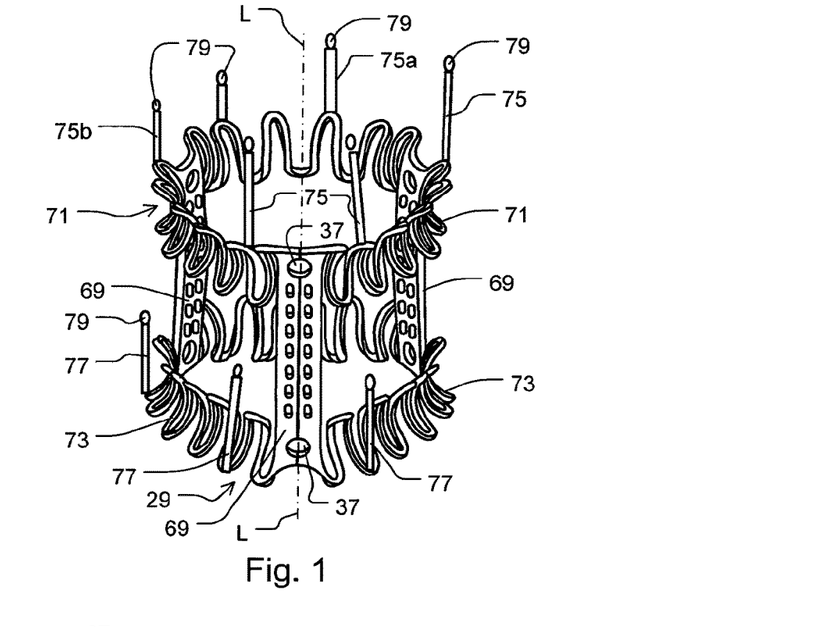
FIG. 1 is a perspective view of a stent for a replacement heart valve shown in its fully retracted or collapsed orientation in a first embodiment.
Figure 1A:
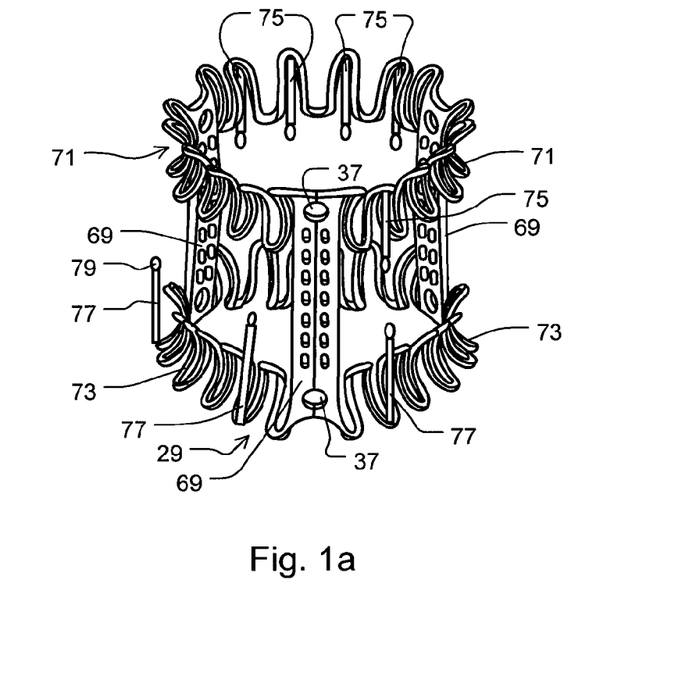
FIG. 1a is a perspective view of a stent for a replacement heart valve like the one of FIG. 1 in its fully retracted or collapsed orientation in a second embodiment.

A first preferred embodiment of a tubular stent 29 incorporating various features of the invention is shown in FIG. 1 through FIG. 6 whereas FIG. 1a shows another preferred embodiment. The tubular stent 29 has a tubular deployment form with a longitudinal axis L and is optionally surrounded with a covering layer of biocompatible thin sheet material (not shown). It is designed to be deployed in a collapsed condition using a delivery implement where it is slidably disposed within or on a catheter that is caused to enter the body through a vein or through a cannula implanted intercostally in the chest, through which it is directed through a atrial wall or the left ventricular wall of the heart and, for example, and then through the orifice of the mitral valve.

The tubular stent 29 can be made of wire-like material, which may be of circular, square, rectangular, oval or other cross section, of a shape-alloy material which has sufficient elasticity such that it can be manually crimped or contracted by applying radially inward directed forces to reduce the diameter of the tubular structure. More specifically, the tubular stent 29 is preferably made of a suitable metal or polymeric material that is biocompatible and has shape-memory properties. Parts of the stent or the complete stent can be resorbable. However, it is more preferably made of a Nitinol alloy that has an activation temperature (Af) below normal body temperature of about 37° C.; thus, the radial force it will exert in tending to return to its "memory" shape can be controlled by varying the temperature difference between the Af and the temperature at which it will be deployed. The individual elements of the overall filamentous construction will usually have a square, rectangular, round or oval cross section that results from polishing after the structure has preferably been laser-cut from a single tube having an appropriate diameter proportional to the desired final valve size. After such cutting, the tubular stent 29 is formed to take its ultimate desired final shape and then treated with heat to set its "memory" so it will always return to this shape. By appropriately selecting a Nitinol alloy and processing it, the tubular stent 29 will have super-elastic properties at and below normal body temperature so it will exhibit sufficient flexibility to allow it to be manipulated. Accordingly, as the tubular stent 29 gradually warms to body temperature, the tubular stent 29 slowly assumes its desired folded-over final shape which is shown in FIG. 2.

Illustrated in FIGS. 1 through 2 is a preferred embodiment of a tubular stent 29 that is designed to be incorporated as a part of a bioprosthetic heart valve. The tubular stent 29 is made of shape-memory material and is constructed to allow it to be expanded and/or contracted to exhibit different diameters. Basically, the stent 29 includes a proximal or apical ring (or ring portion) 71 and a basal or proximal ring (or ring portion) 73, with multiple, in particular three, longitudinally extending posts 69, the ends of which are incorporated into these two, spaced-apart rings 71, 73 of the stent 29. The posts 69 are located equiangularly at 120° to one another by way of example. The posts 69 are equally long by way of example. The rings and the posts may be formed of generally wire form material as described hereinbefore with respect to the tubular stent 29; however, the stent 29 is again preferably laser-cut cut from a tube. Both rings are again of undulating design having proximal and distal tips, with the proximal ring 71 preferably having optionally slightly deeper loops. In the undulating shape a plurality of loops can be arranged in generally sine wave fashion and extending in opposite directions as distal and proximal tips at each ring. The posts 69 may separate these two, spaced-apart rings 71, 73. The posts 69 may be the only elements (apart from the leaflets or other cover material) or metal or shape-memory elements that separate the rings 71, 73 or interconnect them with each other. The posts 69 may not be part of a mesh. The posts may not have an undulating structure themselves or at least not the undulating structure of one of the rings 71, 73.

Circular apertures 37 are optionally provided near each end of the three posts; these facilitate the routing of control cords or strings for folding the stent 29.

The construction is such that a plurality of distal arms 77 extend from certain of the spaced apart tips of the basal or distal ring 73 or any other section thereof, and a plurality of proximal arms 75 extend from tips of the apical or proximal ring 71 or any other section thereof. In some embodiments according to the present invention, both the distal arms 77 and the proximal arms 75 extend into the same direction in an undeployed or crimped state of the tubular stent 29. In the example of FIG. 1, the direction is towards the top of FIG. 1, i. e. from distal to proximal.

In the exemplary embodiment of FIG. 1 through FIG. 3 the distal arms 77 are attached to distal tips of the distal or basal ring 73 only whereas the proximal arms 75 are attached to proximal tips of the top or proximal ring 71 only. This, however, is not meant as limiting.

Optionally provided—possibly apertured—tabs or eyelets 79 at the ends of both sets of arms 75, 77 again provide locations for the routing of sets of strings that are used, as explained hereinbefore, to control or reverse the shape-memory movement of the arms.

Optionally, as shown in FIG. 1, the proximal arms 75 can be of different length. For example, arm 75a is longer than arm 75b. That way, the brim 91, see FIG. 4 and FIG. 5 can be adapted to the particular conditions of the annulus into which the tubular stent 29 is to be implanted and which has to be sealed for avoiding blood reflux. Hence, it might be of advantage to have arms 75 that or longer than other distal arms 75.

Optionally, as can be seen in FIG. 1a, the proximal arms 75 can be arranged so as to extend towards the distal end of the tubular stent 29 in a folded or crimped state. In consequence, once the tubular stent 29 is being deployed or unfolded, the proximal arms 75 will swing up into their position shown in FIG. 2. This is in contrast to the first embodiment of FIG. 1 where the proximal arms 75 swing downwardly once released form external stress or force. The exemplary embodiment of FIG. 1a allows to have a relatively short folded tubular stent body 29 when compared to that of FIG. 1 with proximal arms extending upwards in the crimped state (with an identical height to that of FIG. 1 in the deployed state). This advantageously contributes to an easy maneuvering of the tubular stent 29 when it is advanced by means of a catheter or the like.

In FIG. 1a, the proximal arms 75 are attached to the distal tips of the proximal ring 71 by way of example. However, they might be attached to the proximal tips of the proximal ring 71 in lieu, similar to what is shown in FIG. 1.

To provide leaflets for the valvular device, flexible sheet material 39, e.g. pericardium, is preferably wrapped around sections of the proximal or basal ring structure 71, 73 to completely surround the ring portions between the posts 69 so that it extends distally interior of the ring within the stent 29 to form the leaflets (not shown). The distal or basal ring 73 of the stent 29 is formed, as can be seen in each FIGURE, have an outwardly concave C-shape contour. It essentially defines a partial toroidal surface as its circumference. The posts 69 have rows of parallel apertures 43 extending throughout their length through which chords or ties are passed the leaflets (not shown) in place within the interior of the stent 29 to create a working valve. Any suitable leaflet designs and attachment may be employed, such as those well-known in this art. In general, leaflets of any of the general types shown in the following three Published U.S. Applications may be used: Nos. 2005/0075731; 2005/0113910; and 2005/0203617, the disclosures of which are incorporated herein by reference. If desired, pledges can be provided to reinforce the leaflets where there is attachment to the posts 69.

In some exemplary embodiment according to the present invention, some or all of the leaflets are made of any artificial not biological material e.g. PTFE. In others, they are made of bioresorbable material that will be replaced by the body own tissue and cells over time.

To implant the tubular stent 29 it is, in its tubular deployment form as shown in FIG. 1, positioned about the exterior surface of a tubular delivery implement 47 (see FIG. 8), and the assembly is loaded into the distal end of a catheter (not shown).

FIG. 2 shows the tubular stent 29 of FIG. 1 in a fully expanded state with no force or stress acting on the tubular stent material. As can be seen, the proximal arms 75 are lowered below a horizontal line (with respect to the illustration of FIG. 2). Hence, the angle $\alpha$ between the distal arms 75 of FIG. 1 and the posts 69 may be about 70° or between 60° and 105°, preferably between 60° and 85°.

FIG. 3 is a cross-sectional view taken generally along the line 7-7 of FIG. 2. Hence, FIG. 3 shows the tubular stent 29 of FIG. 1 in a fully expanded state with no force or stress acting on the tubular stent material. As can be seen in FIG. 3, there is a gap d1 between the outer or most radial end of the proximal tip or tips of the distal ring 73 and the distal arms 77. As can be seen in more detail in FIG. 3a, the positions of the distal arms 77 with respect to, e. g. the posts 69, do change while deploying or crimping. However, the relative positions of the distal arms 77 with respect to the outer or radial end of the proximal tips do not change (nor substantially do not change). Therefore, the gap does not change or is not meant or intended to change upon crimping, deploying and the like. Hence, the distance d1 is—at least more or less—maintained while implanting the tubular stent 29. In any case, there will remain a gab during implanting.

While implanting the tubular stent 29, the gap d1 is used for entangling or catching native structures of the heart as mentioned herein. That way, the distal arms 77 and the gap d1 together act as a hook for hooking the tubular stent 29 to native structures. That way, the tubular stent 29 is prevented from entering from the left ventricle into the left artrium once hooked to, e. g., chordae tendineae.

Figure 3A:
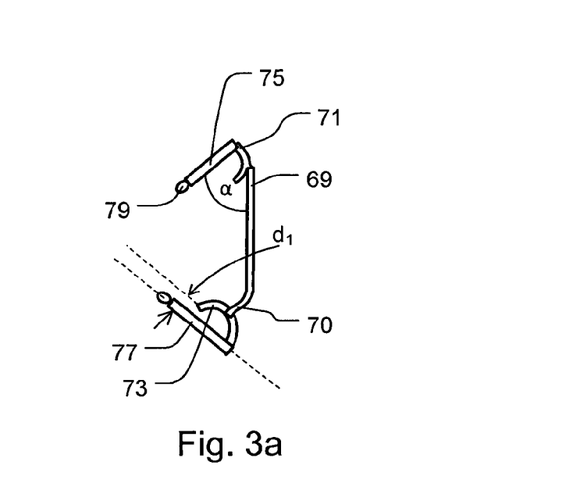
FIG. 3a is a cross-sectional view taken generally along the line 7-7 of FIG. 2 in a non-fully deployed state.

FIG. 3a shows the tubular FIG. 2 in a non-fully deployed state. As can be seen, although the angle between the posts 69 and the distal arms 77 has markedly be widened, the gap d1 has not changed.

When comparing FIG. 3 with FIG. 3a, upon deploying the tubular stent 29, the distal ring 73 or the particular undulations that form the distal ring 77, appear to be tilted or rotated about an imaginary rotation axis 70 extending into the drawing plane of FIG. 3 and FIG. 3a.

When comparing FIG. 1, FIG. 2, FIG. 3 and FIG. 3a with regard to the opening angles of proximal arms 75 and distal arms 77, it becomes apparent that the tubular stent 29 may be used to clamp the native valve or parts thereof which are still connected to the orifice or annulus during implantation between proximal arms 75 and distal arms 77 both of which are arranged on the tubular stent 29 (and made of suitable material having, e. g., shape-memory capacity) so as to approach each other whenever possible. In particular, the proximal arms 75 may exert a longitudinal force onto the tubular stent body, pulling it into the left atrium. The distal arms 79 that hook to the leaflet free edge and chordae tendineae prevent the tubular stent 29 from moving into the left atrium. Hence, the proximal arms 75 and the distal arms 77 may act like a rivet when it comes to fixing the tubular stent 29 in the orifice or annulus.

Figure 4:
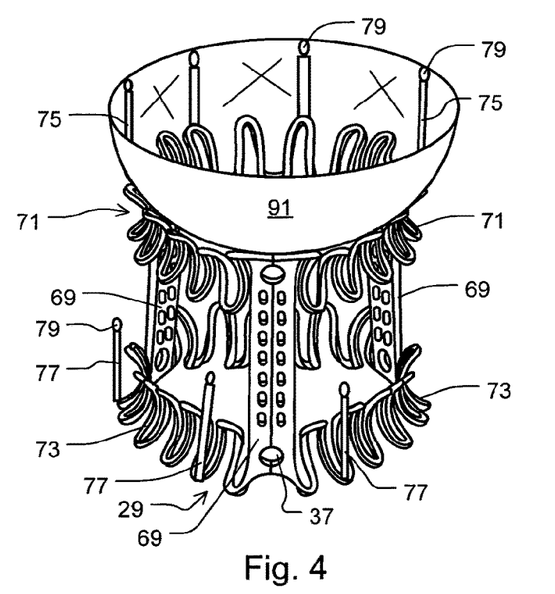
FIG. 4 corresponds to FIG. 1 and shows the stent of FIG. 1 with an additional brim.
Figure 5:
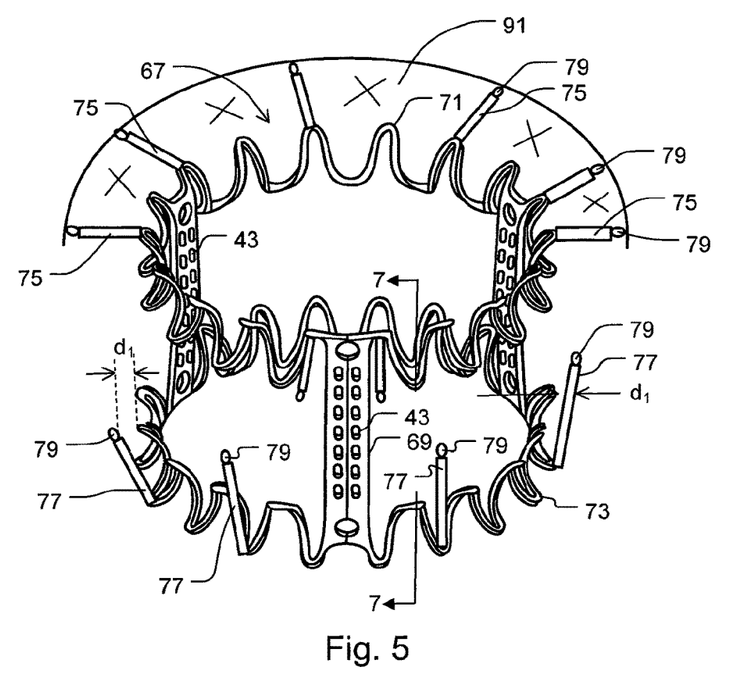
FIG. 5 corresponds to FIG. 2 and shows the stent of FIG. 1 with an additional brim.

FIG. 4 corresponds to FIG. 1, FIG. 5 corresponds to FIG. 2. They show the tubular stent 29 of FIG. 1 and FIG. 2, respectively. They differ from FIG. 1 and FIG. 2 in that they additionally disclose a rim or brim 91 that is attached to the proximal arms 75. It is noted that no mitral valve leaflets are shown in any of the FIGURES. They are omitted for the sake of clearness and readability only. Also, in FIG. 5 only one half of the brim 91 is illustrated.

As is exemplary shown in FIG. 4 and FIG. 5, the brim 91 is supported by the proximal arms 75 along their entire or almost entire length. In the example of FIG. 4 and FIG. 5, the arms 75 are in contact with the brim 91 by their lower or outer surfaces. However, they might also contact the brim 91 by their upper or inner surfaces, or by both the upper and the lower surfaces. In some exemplary embodiments according to the present invention, the arms 75 are covered by the brim material on both of their sides. The arms 75 may, hence, be sandwiched between two layers of brim material.

Figure 6:
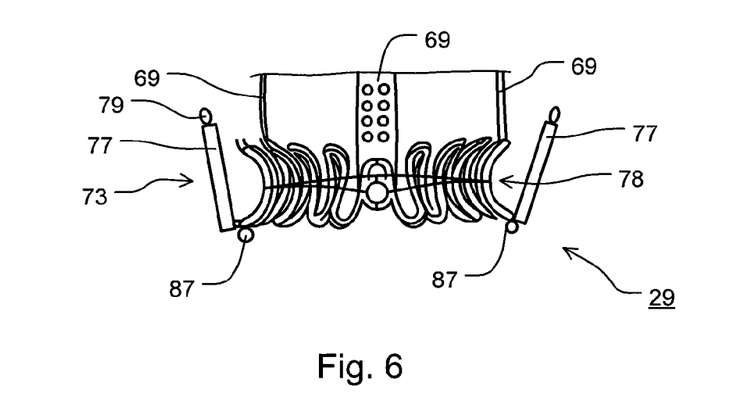
FIG. 6 shows one exemplary embodiment according to the present invention comprising means for departing the tips of distal arms from the tubular stent body or from a longitudinal center line of the tubular stent.

FIG. 6 shows how the arms 77 of the distal or basal ring structure 73 can be forced to assume a less everted position when compared to their crimped or their undeployed position. For the ease of understanding, only two exemplary lateral arms 77 are shown. Obviously, the arms 77 can been forced to lower initially to a lower or more horizontal orientation compared to the one shown in FIG. 6 where the arms 77, at their fee ends, are departed from the tubular main body of the stent 29. The force to do so is effected by, for example, a string 78 guided around the ring structure 73 that distorts the shape of the ring structure such that its distal end or opening of the distal ring 73 is narrower or smaller (not illustrated in FIG. 6 though) than the proximal end or opening of the distal ring 73. In order to amplify the effect of the string 78 it might be arranged closer to the distal end of the distal ring structure 73 than what is shown in FIG. 6 where the string 78 is more or less in the middle of ring 73. In order to keep the string 78 closer to the distal end of the ring structure 73 than to the middle, retaining means such as apertures 87 for the string 78 might be provided, e. g. on the ring structure 73 itself. Also, such optional retaining means might be arranged to guide the string 78 on an inner side of the ring 73 or on an outer side or on a distal front side thereof. FIG. 6 shows how such apertures could be arranged at the distal front side of the distal ring 73, see reference numeral 87. Of course, more than just two such apertures 87 can be provided as well.

The string 78 may be purse-like wound. It may be guided as shown in FIG. 6, or at any other suitable position, for example through a number of apertures 87 that are provided on all or at least some of the distal tips of the distal ring structure 73.

By pulling the string 78, the distal ring 73 will tilt or rotate as indicated in FIG. 3a. Obviously, in FIG. 6 the string 78 is released, no tension is applied onto distal ring 73 by it.

By means of the string 78, in some exemplary embodiments, the tubular stent 29 or parts thereof can be folded. Once the tubular stent 29 is positioned and anchored and the implantation is regarded successful, one may remove the string 78 by disconnecting one end thereof and pulling back the other end.

Figure 7:
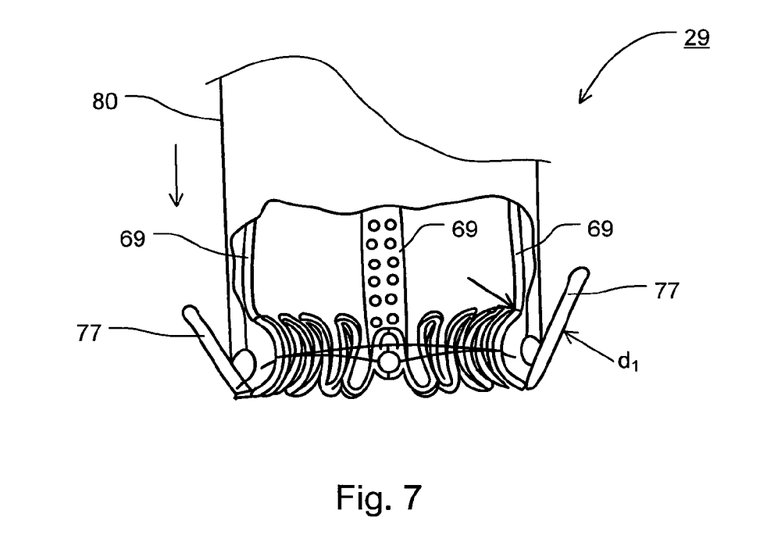
FIG. 7 shows an alternative embodiment to the one shown in FIG. 6 with respect to generating a force that temporarily departs the tips of the distal arms from the tubular stent body or from a longitudinal center line of the tubular stent.

FIG. 7 shows an alternative embodiment to the one shown in FIG. 6 with respect to generating a force that temporarily departs the tips of free ends of the arms 77 from the tubular stent 29 body. In FIG. 7, a suitable, preferably flexible, pusher 80—or a tip of an optional sleeve, if hard enough—is pushed in the direction of the arrow against the arms 77, preferably close to where they are attached to the distal ring structure 73. The pusher 80, which is shown partly cut, may be arranged so as to be slidable within the implement 47 or relative to the latter. In the embodiment of FIG. 7, it is the pusher that forces the distal ring 73 to tilt or rotate which results in distal arms 77 deviating from the tubular main body or the posts 69 while maintaining the gap d1.

Figure 8:
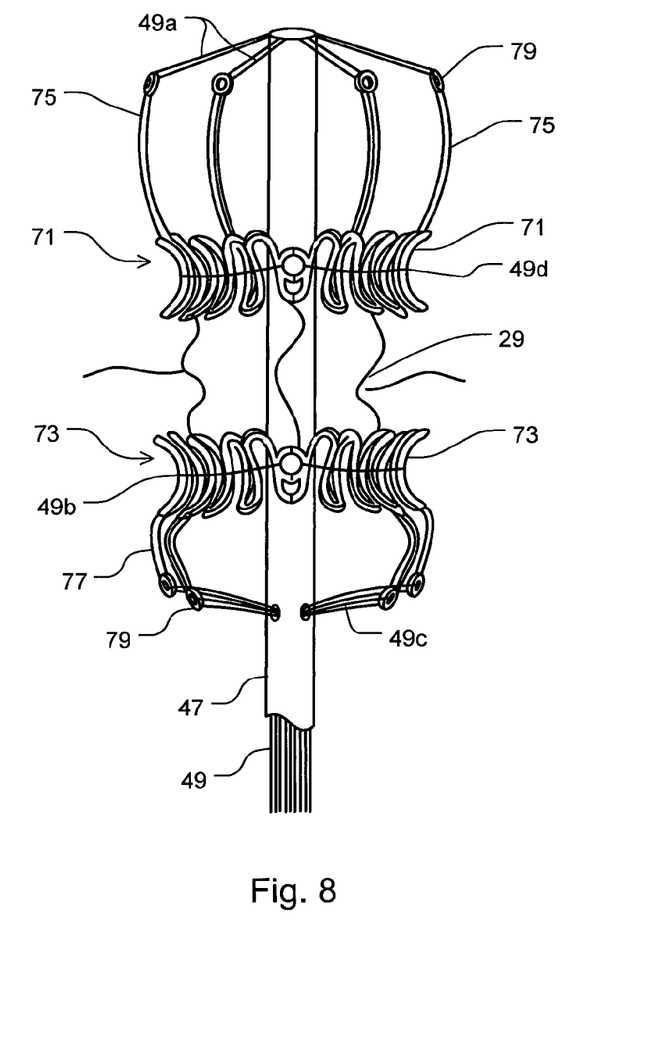
FIG. 8 shows yet another alternative embodiment to the one shown in FIG. 6 with respect to generating a force that temporarily departs the tips of the distal arms from the tubular stent body or from a longitudinal center line of the tubular stent.

FIG. 8 shows yet another alternative embodiment to the one shown in FIG. 6 with respect to generating a force that temporarily departs the tips or free ends of the arms 77 from the tubular stent body of which only its distal ring 73 and its proximal ring 71 are shown for enhanced clarity. Also, the tubular stent 29 is shown attached to the delivery or implanting device 47, for example to a catheter or a catheter tip. Strings 49 that are used for expanding and deploying of the tubular stent 29 as strings 49b and 49d and, in this particular embodiment of FIG. 8 also as strings 49a and 49c for acting on at least one of arms 75 and arms 77, are also shown. They are all slidably routed through the catheter 47 or around rings 71 and 73 and, optionally, through eyelets or apertures 79 of arms 75 or 77. In the particular embodiment shown in FIG. 8 the gap d1 is obviously not maintained.

The solutions of FIG. 6 through FIG. 8 allow for opening up the angle between the arms 77 and the tubular stent body for temporarily holding down the arms 77. In doing so, they allow the tubular stent 29 to become wider than the native mitral valve orifice in the heart by means of its arms 77. If carefully retracted with opened up arms 77, the tubular stent 29 is pressed or pulled against the native mitral valve leaflets pressed against the heart muscle forming a ring. Also, arms 77 are entangled and captured by the confluence of tendinous rope-like elements, known as chordae tendineae. As a result, the tubular stent 29 is stuck. Noticing this with his hands while carefully pulling or proximally advancing the catheter, which carries the tubular stent 29, out of the ventricle, the surgeon knows that the tubular stent 29 has reached its final position within the heart. This can be confirmed by imaging techniques.

Once the tubular stent 29 is no longer confined at all by the catheter sleeve, and with the arms 77 now hooked to structures inside the ventricle such as the chordae tendineae, the proximal arms 75 begin to expand radially outward into a more or horizontal position. If strings 49a are provided, the will be released by the surgeon so as to allow the arms 75 to lower.

In many exemplary embodiments according to the present invention, the opening angle between distal arms 77 and the longitudinal axis of the tubular stent 29 or the posts 69 thereof is between 35° to 70° or any value in between.

A "horizontal position" as used herein refers to the illustrations of the FIGURES where the main body of the tubular stent 29 is shown as vertical; it goes without saying that "horizontal" relates to a line or plane that is rectangular to the longitudinal axis of the stent body or to the posts 69.

If before cutting the loops of string 49b, 49d it should be found that the desired location within the native mitral valve had not been obtained, the tubular stent 29 can still be withdrawn from the mitral valve so long as the loops 49b, 49d are attached.

Once it has been finally ascertained that the positioning and functioning of either of these implanted valves are satisfactory by observing valve function, leaflet mobility, transvalvular gradient and regurgitation using transesophageal echocardiography, the procedure is terminated. The delivery device is removed, and the vein or the wall of the heart is securely closed.

Although the invention has been described with regard to certain preferred embodiments which constitute the best mode known to the inventors for carrying out this invention, it should be understood that various changes and modifications as would be obvious to one of ordinary skill in the art may be made without deviating from the scope of the invention which is set forth in the claims appended hereto.

Particular features of the invention are emphasized in the claims that follow.

The invention claimed is:

1. A collapsible-expandable tubular stent constructed of shape-memory material which is implantable into a human heart, which comprises: proximal and distal rings and at least two spaced apart posts that extend axially between said rings;
   said distal ring comprising a plurality of distal arms which are connected to the distal ring at only one end of the arm and which have a free opposite end;
   said proximal ring comprising a plurality of proximal arms, which are connected at only one end of the arm to the proximal ring and which have a free opposite end, which proximal arms are constructed to swing radially outward at their free ends or to move radially outward, in particular when first put in parallel with a longitudinal axis of the tubular stent by means of a radially inwardly acting force with the force then being released, or to exert from the longitudinal axis of the tubular stent by an angle between 60° and 105°;
   wherein the distal arms are attached to the distal ring or part of the latter such that a gap is provided between a proximal section or circumference or envelope of an undulating pattern of the distal ring or section thereof and the distal arm, and
   wherein the tubular stent is produced such that the gap does not widen or become narrower upon deploying the tubular stent from a crimped state, or such that the gap keeps its width upon deploying.

2. A collapsible-expandable tubular stent according to claim 1, wherein the distal arms are connected to the distal end or distal tips of the distal ring.

3. A collapsible-expandable tubular stent according to claim 1, wherein the proximal arms are connected to the proximal end or proximal tips of the proximal ring.

4. A collapsible-expandable tubular stent according to claim 1, wherein at least some of said distal arms and/or some of the proximal arms have apertures at its said free opposite end which allows attachment of strings to individually control and retract some or each of said arms.

5. A collapsible-expandable tubular stent according to claim 1, wherein at least some of said proximal arms are intended to assume a more or less rectangular position with regard to a longitudinal axis of the tubular stent.

6. A collapsible-expandable tubular stent according to claim 1, wherein at least some of said proximal arms are interconnected to a brim of biocompatible material.

7. A collapsible-expandable tubular stent according to claim 1, wherein the distal ring is arranged so as assume a smaller diameter at its distal end than a its proximal end if the free ends of the distal arms are being forced to further extend radially away from the longitudinal axis or from a longitudinal centre line of the tubular stent.

8. A heart valve comprising a the tubular stent according to claim 1, the tubular stent being interconnected to a plurality of flexible leaflets disposed interior of said stent, which leaflets open to permit blood flow in a downstream direction and close to prevent blood flow in an upstream direction therethrough.

9. A heart valve according to claim 8, wherein the leaflets are arranged so as to form a first cusp, a second cusp and a third cusp.

10. A heart valve according to claim 8, the stent being connected with an exterior covering of biocompatible sheet material surrounding the posts.

11. A heart valve according to claim 8, being a mitral heart valve.

12. A delivery system for delivering a heart valve to a patient's heart, the system comprising a heart valve according to claim 8.

* * * * *